US010773421B2

(12) United States Patent
Konishi et al.

(10) Patent No.: US 10,773,421 B2
(45) Date of Patent: Sep. 15, 2020

(54) METHOD FOR MANUFACTURING RECYCLED PULP FROM USED SANITARY ARTICLE

(71) Applicant: Unicharm Corporation, Ehime (JP)

(72) Inventors: Takayoshi Konishi, Kagawa (JP); Toshio Hiraoka, Kagawa (JP)

(73) Assignee: Unicharm Corporation, Ehime (JP)

( * ) Notice: Subject to any disclaimer, the term of this patent is extended or adjusted under 35 U.S.C. 154(b) by 431 days.

(21) Appl. No.: 15/516,260

(22) PCT Filed: Sep. 28, 2015

(86) PCT No.: PCT/JP2015/077358
§ 371 (c)(1),
(2) Date: Mar. 31, 2017

(87) PCT Pub. No.: WO2016/059964
PCT Pub. Date: Apr. 21, 2016

(65) Prior Publication Data
US 2017/0305037 A1    Oct. 26, 2017

(30) Foreign Application Priority Data
Oct. 15, 2014  (JP) ................................. 2014-211191

(51) Int. Cl.
| B29B 17/02 | (2006.01) |
| B09B 3/00 | (2006.01) |
| D21C 5/02 | (2006.01) |
| D21C 9/00 | (2006.01) |
| C08J 11/16 | (2006.01) |
| A61L 11/00 | (2006.01) |
| A61L 2/16 | (2006.01) |
| A61L 2/18 | (2006.01) |
| D21C 9/153 | (2006.01) |
| D21C 3/04 | (2006.01) |
| A61F 13/15 | (2006.01) |
| B29L 31/48 | (2006.01) |

(52) U.S. Cl.
CPC ............... *B29B 17/02* (2013.01); *A61L 2/16* (2013.01); *A61L 2/18* (2013.01); *A61L 2/183* (2013.01); *A61L 11/00* (2013.01); *B09B 3/00* (2013.01); *B09B 3/0075* (2013.01); *C08J 11/16* (2013.01); *D21C 3/04* (2013.01); *D21C 5/02* (2013.01); *D21C 9/00* (2013.01); *D21C 9/153* (2013.01); *A61F 13/15* (2013.01); *B29B 2017/0289* (2013.01); *B29L 2031/4878* (2013.01); *Y02W 30/622* (2015.05); *Y02W 30/648* (2015.05)

(58) Field of Classification Search
None
See application file for complete search history.

(56) References Cited

U.S. PATENT DOCUMENTS

| 5,684,756 A * | 11/1997 | Schmitz ................. G01L 11/04 367/188 |
| 2015/0291762 A1* | 10/2015 | Watanabe ......... A61F 13/15707 428/401 |
| 2016/0237617 A1* | 8/2016 | Yamaguchi .............. D21C 5/02 |

FOREIGN PATENT DOCUMENTS

| EP | 3 064 644 A1 | 9/2016 |
| JP | 4-317785 | 11/1992 |
| JP | H06-9721 | 1/1994 |
| JP | 8-209191 | 8/1996 |
| JP | A 09-067797 A | 3/1997 |
| JP | 2001-047023 A | 2/2001 |
| JP | 2001-310178 A | 11/2001 |
| JP | 2009-183893 A | 8/2009 |
| JP | 2013-056326 A | 6/2013 |
| JP | 2013-150976 A | 8/2013 |
| JP | 2014-161749 A | 9/2014 |
| KR | 101044439 B1 | 6/2011 |
| WO | WO 2014/007105 A1 | 1/2014 |
| WO | WO 2014/041251 A1 | 3/2014 |
| WO | WO 2014/168179 A1 | 10/2014 |

OTHER PUBLICATIONS

Li Guang, editor, "Polymer Material Processing Technology", *China Textile & Apparel Press*, 5th printing, Feb. 2010 (9 pages).
Shuichi Matsumura et al., "Miscellaneous Biopolymers and Biodegradation of Synthetic Polymers", *Chemical Industry Press*, 1st Edition, Mar. 2005 (6 pages).
Nakaoka, Hiroko et al., *Recovery Technology of Pulp Component in Used Disposable Diapers Utilizing Ozone De-watering Treatment of Highly-Absorbent Polymer Utilizing Ozone*, Abstracts of the 64th Annual Meeting of the Japan Wood Research Society, K14-08-1315, Mar. 13, 2014 with English translation ((6 pgs).
International Search Report from corresponding PCT application No. PCT/JP2015/077358 dated Dec. 8, 2015 (4 pgs).

* cited by examiner

*Primary Examiner* — Jacob T Minskey
(74) *Attorney, Agent, or Firm* — Osha Liang LLP

(57) ABSTRACT

The present invention addresses the problem of efficiently manufacturing a recycled pulp from a used sanitary article, said recycled pulp being reusable for sanitary articles and having an ash content and antibacterial properties both meeting the standards for sanitary articles. A method for manufacturing a recycled pulp reusable for sanitary articles by recovering a pulp fiber from a used sanitary article that contains the pulp fiber and a high water-absorbing polymer, said method comprising an ozone treatment step for immersing the used sanitary article or pulp fiber in an ozone-containing aqueous solution and thus disintegrating the high water-absorbing polymer contained in the used sanitary article or sticking to the pulp fiber, characterized in that the used sanitary article or pulp fiber is treated with a cationic antibacterial agent before, after or together with the ozone treatment step.

19 Claims, No Drawings

METHOD FOR MANUFACTURING RECYCLED PULP FROM USED SANITARY ARTICLE

RELATED APPLICATION

This application is a 35 U.S.C. § 371 national phase filing of International Patent Application No. PCT/JP2015/077358, filed Sep. 28, 2015, through which and to which priority is claimed under 35 U.S.C. § 119 to Japanese Patent Application No. 2014-211191, filed Oct. 15, 2014, the complete disclosure of which is hereby expressly incorporated by reference.

TECHNICAL FIELD

The present invention relates to a method for manufacturing recycled pulp from a used sanitary article. More particularly, the present invention relates to a method for manufacturing recycled pulp able to be reused in sanitary articles by recovering pulp fiber from used disposable diapers or other sanitary articles containing pulp fiber and a superabsorbent polymer.

BACKGROUND ART

Efforts are currently being made to recycle used disposable diapers and other sanitary articles. For example, Patent Document 1 discloses a method for treating used disposable diapers comprising efficiently separating a used disposable diaper and washing with water while sequentially transferring the used diaper from a first-stage washing tub to a second-stage washing tub using a continuous washing machine having a plurality of washing tubs arranged in series to enable constituent materials thereof to be reused. According to the method described in Patent Document 1, in addition to using hypochlorous acid for primary disinfection of the used diaper (Paragraph [0044]), superabsorbent polymer present in the disposable diaper is dehydrated using lime (Paragraph [0047]), and the chlorine component of the hypochlorous acid is removed from the used diaper in a rinsing step (Paragraph [0046]).

PRIOR ART DOCUMENTS

Patent Documents

Patent Document 1: Japanese Unexamined Patent Publication No. 2009-183893

DISCLOSURE OF THE INVENTION

Problems to be Solved by the Invention

Hypochlorous acid is used for primary disinfection in the method described in Patent Document 1. However, the use of sanitary products made of materials using hypochlorous acid is prohibited by sanitary material industry standards, thereby preventing the resulting recycled pulp from being reused in sanitary products. In addition, since the chlorine component is removed in a rinsing step and is not allowed to remain in the pulp, the resulting recycled pulp lacks antibacterial properties, and ends up rotting unless dried. In addition, the superabsorbent polymer dehydrated using lime is transformed into a solid powder having a particle size of several micrometers to several hundred micrometers, and these fine particles easily become trapped between the pulp fibers, thereby preventing them from being completely removed by physical washing alone. When attempting to reuse recycled pulp recovered in this manner, not only does residual superabsorbent polymer end up becoming a contaminant, but since it is in the form of a calcium salt, there is increased likelihood of ash being detected in the recovered pulp fiber at a level that exceeds sanitary article standards. In addition, since the use of ash results in strong alkalinity, ozone is easily deactivated in the case of subjecting the recycled pulp to ozone treatment.

An object of the present invention is to efficiently manufacture recycled pulp, which can be reused in sanitary articles and has ash content and antibacterial properties that comply with sanitary article standards, from a used sanitary article.

Means for Solving the Problems

The present invention is a method for manufacturing recycled pulp able to be reused in sanitary articles by recovering pulp fiber from a used sanitary article containing pulp fiber and superabsorbent polymer, wherein the method comprises an ozone treatment step for decomposing superabsorbent polymer present in the used sanitary article or adhered to the pulp fiber by immersing the used sanitary article or pulp fiber in an ozone-containing aqueous solution, and the used sanitary article or pulp fiber is treated with a cationic antibacterial agent either before, simultaneous to or after the ozone treatment step.

In the present invention, the ash content of recycled pulp obtained according to the aforementioned method is 0.65% by weight or less.

The aforementioned method preferably comprises a decomposition step for decomposing a used sanitary article into pulp fiber and other materials by allowing physical force to act on the used sanitary article in an aqueous solution containing a polyvalent metal ion or an acidic aqueous solution having a pH of 2.5 or lower prior to the ozone treatment step.

The aforementioned method preferably comprises a step for washing a used sanitary article and decomposing the used sanitary article into constituents thereof by agitating the used sanitary article in an aqueous solution containing a disinfectant or water after the ozone treatment step.

In the aforementioned method, the aqueous solution containing a polyvalent metal ion or the acidic aqueous solution having a pH of 2.5 or lower preferably contains a cationic antibacterial agent.

In the aforementioned method, the aqueous solution containing a disinfectant or the water preferably contains a cationic antibacterial agent.

In the aforementioned method, the ozone-containing aqueous solution preferably contains a cationic antibacterial agent.

In the aforementioned method, the cationic antimicrobial agent is preferably a quaternary ammonium salt.

In the aforementioned method, the ozone-containing aqueous solution preferably contains an organic acid and the pH of the ozone-containing aqueous solution is 2.5 or lower.

In the aforementioned method, the concentration of ozone in the ozone-containing aqueous solution is preferably 1 ppm by weight to 50 ppm by weight.

In the aforementioned method, the polyvalent metal ion is preferably an alkaline earth metal ion.

In the aforementioned method, the recycled pulp preferably has an antibacterial activity value of 2.0 or more.

Effects of the Invention

According to the present invention, recycled pulp having ash content and antibacterial properties that comply with sanitary material standards can be manufactured from a used sanitary article by combining ozone treatment and antibacterial treatment.

MODE FOR CARRYING OUT THE INVENTION

The present invention relates to a method for manufacturing recycled pulp capable of being reused in a sanitary article by recovering pulp fiber from a used sanitary article containing pulp fiber and superabsorbent polymer.

There are no particular limitations on the sanitary article provided it contains pulp fiber and superabsorbent polymer, and examples thereof include disposable diapers, urinary incontinence pads, urine collection pads, sanitary napkins and panty liners. Among these, urinary incontinence pads and disposable diapers collectively recovered at health care institutions and the like are preferable from the viewpoint of greater ease when separating garbage and having a comparatively high pulp content.

There are no particular limitations on the pulp fiber, and examples thereof include fluff pulp fiber and chemical pulp fiber.

The superabsorbent polymer (SAP) has a three-dimensional mesh structure obtained by suitably crosslinking a water-soluble polymer, and although it is capable of absorbing several ten to several hundred times its weight of water, it is essentially water-insoluble, and water that has been absorbed is not released unless a certain degree of pressure is applied, with example thereof including starch-based, acrylic acid-based and amino acid-based particulate and fibrous polymers.

In this description, pulp manufactured according to the method of the present invention is referred to as "recycled pulp".

The method of the present invention comprises an ozone treatment step for decomposing superabsorbent polymer present in a used sanitary article or adhered to pulp fibers by immersing the used sanitary article or pulp fiber in an ozone-containing aqueous solution.

In this step, the superabsorbent polymer is decomposed, lowered in molecular weight and solubilized. Here, the state in which a superabsorbent polymer has been decomposed, lowered in molecular weight and solubilized refers to the state in which it can pass through a 2 mm screen mesh. Namely, in this step, the superabsorbent polymer is decomposed to a degree that allows it to pass through a 2 mm screen mesh.

The ozone-containing aqueous solution used in this step refers to an aqueous solution in which ozone has been dissolved therein. The ozone-containing aqueous solution can be prepared using, for example, an ozone water generator (such as the OS-25V Ozone Generator manufactured by Mitsubishi Electric Corp. or the ED-OWX-2 Ozone Water Exposure Tester manufactured by EcoDesign, Inc.).

Although there are no particular limitations on the ozone concentration of the ozone-containing aqueous solution provided it is a concentration that enables decomposition of the superabsorbent polymer, it is preferably 1 ppm by weight to 50 ppm by weight, more preferably 2 ppm by weight to 40 ppm by weight, and even more preferably 3 ppm by weight to 30 ppm by weight. If the ozone concentration is excessively low, the superabsorbent polymer is unable to be solubilized completely, thereby resulting in the risk of the superabsorbent polymer remaining in the recovered pulp fiber. Conversely, if the ozone concentration is excessively high, in addition to the risk of damaging the pulp fiber due to the increased oxidizing power thereof, there is also the risk of problems with safety.

There are no particular limitations on the duration of immersion in the ozone-containing aqueous solution provided the superabsorbent polymer can be decomposed. The duration of immersion in the ozone-containing aqueous solution may be shortened if the ozone concentration of the ozone-containing aqueous solution is high, while a longer amount of time is required if the ozone concentration of the ozone-containing aqueous solution is low.

The product of the ozone concentration (ppm) of the ozone-containing aqueous solution and the duration (minutes) of immersion in the ozone-containing ozone aqueous solution (to be referred to as the "CT value") is preferably 100 ppm·min to 6000 ppm·min, more preferably 200 ppm·min to 4800 ppm·min, and even more preferably 300 ppm·min to 3600 ppm·min. If the CT value is excessively low, the superabsorbent polymer is unable to be completely solubilized, resulting in the risk of the superabsorbent polymer remaining in the recovered pulp fiber. Conversely, if the CT value is excessively high, there is the risk of damage to the pulp fiber, decreased safety and an increase in the manufacturing cost.

The reason for the duration of immersion in the ozone-containing aqueous solution being dependent on the ozone concentration of the ozone-containing aqueous solution is as was previously described, and is preferably 5 minutes to 120 minutes, more preferably 10 minutes to 100 minutes and even more preferably 20 minutes to 80 minutes.

Although there are no particular limitations on the amount of the ozone-containing aqueous solution provided it enables the superabsorbent polymer to be decomposed, the amount thereof is preferably 300 parts by weight to 5000 parts by weight, more preferably 500 parts by weight to 4000 parts by weight and even more preferably 800 parts by weight to 3000 parts by weight based on 100 parts by weight (dry weight) of the used sanitary article or pulp fiber. If the amount of the ozone-containing aqueous solution is excessively low, the superabsorbent polymer is unable to be completely solubilized, resulting in the risk of the superabsorbent polymer remaining in the recovered pulp fiber. Conversely, if the amount of the ozone-containing aqueous solution is excessively high, there is the risk or this leading to an increase in the manufacturing cost.

Although there are no particular limitations on the method used to immerse the used sanitary article or pulp fiber in the ozone-containing aqueous solution in the ozone treatment step, and as an example thereof, the ozone-containing aqueous solution is placed in a container and the used sanitary article or pulp fiber is then placed in the ozone-containing aqueous solution. The contents of the container may or may not be agitated during immersion. In addition, ozone gas may be bubbled through the ozone-containing aqueous solution placed in the container to generate a gentle current in the ozone-containing aqueous solution with the rising ozone gas bubbles. There are no particular limitations on the temperature of the ozone-containing aqueous solution provided the superabsorbent polymer is able to be decomposed. The ozone-containing aqueous solution may be heated or may be left at room temperature.

In the ozone treatment step, the superabsorbent polymer is subjected to the oxidative decomposition action of the ozone and the three-dimensional mesh structure of the superabsorbent polymer is disrupted, thereby causing the superabsorbent polymer to lose its water retentiveness, decrease in molecular weight and become solubilized. The increased fluidity of the superabsorbent polymer enables it to dissolve in the ozone-containing aqueous solution. In addition, since hot melt adhesive used to join the sanitary article is also subjected to oxidative decomposition by the ozone-containing aqueous solution, adhesive strength between constituents of the sanitary article weakens. Moreover, the used sanitary article is subjected to primary disinfection or the pulp fiber is disinfected, bleached and deodorized in this step.

The ozone-containing aqueous solution is preferably acidic. More preferably, the pH of the ozone-containing aqueous solution is 2.5 or lower, even more preferably 0.5 to 2.5, and still more preferably 1.0 to 2.4. The use of an acidic ozone-containing aqueous solution makes it possible to inhibit initial swelling of the superabsorbent polymer accompanying absorption of water, thereby dramatically improving the effects of decomposing and removing superabsorbent polymer by the ozone, or in other words, the superabsorbent polymer can be decomposed in a short period of time. In the decomposition step to be subsequently described, although the superabsorbent polymer does not swell following absorption of water even if an acidic ozone-containing aqueous solution is not used since the superabsorbent polymer is dehydrated by polyvalent metal ion when an aqueous solution is used that contains a polyvalent metal ion, an aqueous solution having a pH of 2.5 or lower is used to dissolve and remove polyvalent metal adhered to the surface of pulp fiber with acid. On the other hand, the reason for using an aqueous solution having a pH of 2.5 or lower when using an acidic aqueous solution having a pH of 2.5 or lower in the decomposition step is to completely inhibit swelling of the superabsorbent polymer caused by absorption of water. In addition, disinfection effects can also be imparted by treating with an acidic ozone-containing aqueous solution. Incidentally, the principle behind inhibition of swelling of the superabsorbent polymer attributable to absorption of water is thought to be, since negatively charged carboxyl groups of the acidic aqueous solution are neutralized by positively charged hydrogen ions, the ionic repulsive force of the carboxyl groups is weakened, thereby resulting in a decrease in the ability to absorb water. If the pH of the ozone-containing aqueous solution is excessively low, there is the risk of a decrease in the water absorption capacity of the resulting recycled pulp. Although the reason for the decrease in water absorption capacity of the resulting recycled pulp is unclear, it is thought to be the result of denaturation of the pulp fiber per se.

An acidic ozone-containing aqueous solution can be produced by adding acid to an ozone-containing aqueous solution.

Although there are no particular limitations on the acid and an inorganic acid or organic acid can be used, an organic acid is preferable. Since organic acids function in the weakly acidic range and are environmentally friendly, organic acids are preferable from the viewpoints of safety and the burden on the environment. Although there are no particular limitations on the organic acid and examples thereof include tartaric acid, glycolic acid, malic acid, citric acid, succinic acid, acetic acid and ascorbic acid, citric acid is particularly preferable.

The pH of the acidic ozone-containing aqueous solution can be adjusted according to the type of acid and amount added. Although there are no particular limitations on the concentration of organic acid in the acidic ozone-containing aqueous solution provided the pH thereof is within the prescribed range, it is preferably 0.1% by weight to 5.0% by weight, more preferably 0.2% by weight to 3.0% by weight, and even more preferably 0.5% by weight to 2.0% by weight.

In addition, by making the pH to be 2.5 or lower with organic acid, disinfection effects can be enhanced inside a disposable diaper where ozone gas inherently has difficulty in making direct contact.

When using an alkaline calcium compound in the decomposition step to be subsequently described, there are cases in which the alkaline calcium compound remains on the pulp fiber supplied to the ozone treatment step, and when the pulp fiber is added to the ozone-containing aqueous solution, the pH of the ozone-containing aqueous solution may change. In the case the pH of the ozone-containing aqueous solution differs between that prior to addition of pulp fiber and that after the addition thereof, the pH of the ozone-containing aqueous solution here refers to the pH of the ozone-containing aqueous solution after the addition of pulp fiber.

The pH is adjusted by placing the pulp fiber and ozone-containing aqueous solution in a treatment tank, adding acid thereto while stirring, and then discontinuing addition of acid when the pH of the solution in the treatment tank has reached the prescribed pH.

Citric acid is particularly preferable for the acid used in the ozone treatment step.

When using an aqueous solution containing calcium ions in the ozone treatment step, calcium ions and various calcium compounds adhere to the surface of the separated pulp fiber. Since calcium compounds adhered to the pulp fiber are not necessarily water-soluble and may include insoluble or poorly soluble compounds, they cannot be removed by washing with water alone. Since citric acid forms a chelate with calcium resulting in the formation of water-soluble calcium citrate, insoluble or poorly soluble calcium compounds can be effectively dissolved and removed from the surface of the pulp fiber. Since citric acid is also able to form chelates with metals other than calcium, in the case insoluble or poorly soluble metal compounds other than calcium compounds are adhered to the surface of the pulp fiber, not only calcium compounds but also insoluble or poorly soluble metal compounds other than calcium compounds can be dissolved and removed. As a result, the ash content of the resulting recycled pulp can be reduced.

Once ozone treatment has been completed, the ozone-containing aqueous solution is discharged followed by recovery of the used sanitary article or pulp fiber from which the superabsorbent polymer has removed. In this step, superabsorbent polymer that has been decomposed by being dissolved in the ozone-containing aqueous solution is discharged together with the ozone-containing aqueous solution, thereby preventing solid particles of the superabsorbent polymer from remaining in the used sanitary article or pulp fiber. Although there are no particular limitations on the method used to discharge the ozone-containing aqueous solution, as an example thereof, a plug may be provided in the bottom of the container and the ozone-containing aqueous solution may be drained by pulling out the plug, or the used sanitary article may be taken out of the container followed by draining the ozone-containing aqueous solution. In this step, ozone-containing aqueous solution having decomposed superabsorbent polymer dissolved therein is discharged after passing through a 2 mm screen mesh. Since the superabsorbent polymer is decomposed by ozone treatment to a degree that it can pass through a 2 mm screen mesh, the decomposed superabsorbent polymer is discharged in this step together with the ozone-containing aqueous solution after passing through a 2 mm screen mesh.

The method of the present invention comprises treating the used sanitary article or pulp fiber with a cationic antibacterial agent either before, simultaneous to or after the ozone treatment step (to be simply referred to as "antibacterial treatment").

Although examples of cationic antibacterial agents include quaternary ammonium salts, guanidine-based antibacterial agents (such as chlorhexidine gluconate or chlorhexidine hydrochloride), hexetidine and metronidazole, quaternary ammonium salts are preferable.

There are no particular limitations on the quaternary ammonium salt provided it has a quaternary ammonium salt structure in a molecule thereof, and examples thereof include alkyltrimethylammonium salts, polyoxyethylene alkylmethylammonium salts, alkylbenzyldimethylammonium salts, alkylpyridinium salts and quaternary ammonium salts represented by the following formulas (1) to (4):

$$[R(CH_3)_3N^+]_l X \qquad (1)$$

$$[R(CH_3)N^+(CH_2CH_2O)_mH[(CH_2CH_2O)_nH]]_l X \qquad (2)$$

$$[R(CH_3)_2N^+CH_2C_6H_5]_l X \qquad (3)$$

$$[RPy^+]_l X \qquad (4)$$

wherein each R independently represents an alkyl group, each X independently represents a monovalent or divalent anion, each l independently represents an integer of 1 or 2, each m and n independently represent an integer of 2 to 40, and Py represents a pyridine ring.

The alkyl group in the quaternary ammonium salt is preferably a saturated hydrocarbon group having 8 to 18 carbon atoms since it demonstrates remarkable bactericidal action as a result of being a long-chain alkyl group, and is more preferably an octyl group, lauryl group, myristyl group or cetyl group and even more preferably a lauryl group.

The quaternary ammonium salt is a salt formed with a halide ion such as $F^-$, $Cl^-$, $Br^-$ or $I^-$ or that formed with $NO^-$ or $SO_4^{2-}$, and is preferably a salt formed with $Cl^-$ due to its high electronegativity.

Specific examples of preferable quaternary ammonium salts include benzalkonium chloride, cetylpyridinium chloride, benzethonium chloride and dequalinium chloride.

One of these quaternary ammonium salts can be used alone or two or more thereof can be used in combination.

In order to ensure disinfection during recycling treatment and antimicrobial properties of the pulp obtained following treatment without using hypochlorous acid for which use in sanitary articles is prohibited by industry standards, anionic pulp fiber can be selectively adsorbed and antimicrobial properties can be imparted to the pulp fiber per se by disinfecting using a cationic antibacterial agent. In addition, due to the favorable compatibility between the quaternary ammonium salt and citric acid used to inhibit swelling of the superabsorbent polymer, antibacterial action is enhanced by the synergistic effect thereof, thereby making it possible to demonstrate sterilizing effects on viruses and the like for which disinfection is difficult with quaternary ammonium salts alone.

In the case of using benzalkonium chloride or cetylpyridinium chloride for the cationic antibacterial agent, the amount of free antibacterial agent in the treatment solution decreases by 50% to 90% from before to after treatment, with the majority adhering to the anionic pulp fiber to impart antibacterial properties to the pulp.

In addition, although bactericidal effects are imparted to pulp fiber by lime and sodium hypochlorite in Comparative Example 1 to be subsequently described and bactericidal effects are imparted to pulp fiber by citric acid and ozone in Comparative Example 2, resulting in both being positive for antibacterial effects and imparting antibacterial properties to the pulp fiber, since mold was confirmed to grow on the pulp fiber in a short period of time when stored in a damp state, antifungal effects were low, thereby preventing storage in a damp state unless stored completely sealed in a cold location or unless an anti-mold agent was added thereto. In contrast, in the case of the present invention provided with a cationic antibacterial agent, storage was possible in a damp state with no growth of mold observed even after storing for one month. Accordingly, in the case of using pulp fiber obtained as a raw material for the wet production of paper in the manner of tissue paper, the absence of the need for drying eliminates the need for drying equipment, thereby resulting in a compact treatment method that is superior in terms of energy consumption, cost, production time and environmental impact.

Since ozone is short-lasting and loses activity immediately, although pulp fiber is sterilized during treatment, it ends up rotting easily due to adherence of airborne bacteria and the like following treatment, thereby requiring drying or the addition of an antibacterial agent. Since cationic antimicrobial agents are adsorbed to the pulp fiber, the pulp fiber obtained by going through antibacterial treatment demonstrates antibacterial properties, has the characteristic of being resistant to rotting even if stored in a damp state, and does not require drying treatment that consumes a huge amount of energy, thereby enabling the realization of a low burden on the environment, low running cost and reduced equipment size. In addition, since a majority of the cationic antibacterial agent is adsorbed onto the pulp fiber, the residual concentration in wastewater is low, resulting in the characteristic of placing a low burden on wastewater treatment. Since the use of quaternary ammonium salts is permitted in sanitary articles, recycled pulp manufactured with the method of the present invention can be reused in sanitary articles. In addition, it is also able impart antimicrobial properties to sanitary articles depending on the incorporated amount thereof.

Antibacterial treatment can be carried out by immersing a used sanitary article or pulp fiber in an aqueous solution having a cationic antibacterial agent dissolved therein. When carrying out antibacterial treatment simultaneous to the ozone treatment step, the cationic antimicrobial agent is added to the ozone-containing aqueous solution.

The concentration of the cationic antibacterial agent in the aqueous solution having the cationic antibacterial agent dissolved therein is preferably 0.002% by weight or more and more preferably 0.003% by weight or more. In the case the concentration is less than 0.002% by weight, there is the potential for mold to grow in less than 30 days when stored at 30° C. However, since the optimum concentration varies according to the charged amount of used sanitary article or pulp fiber, it is necessary to set the concentration so that free antibacterial agent in the treatment solution after treatment is in excess relative to the amount able to be adsorbed by the pulp so that 10% or more of the amount prior to treatment remains (so that the amount adsorbed by the pulp is 90% or less). The amount relative to pulp fiber is preferably 0.5% by weight or more. If the concentration of the cationic antibacterial agent is excessively high, although antimicrobial activity of the treatment liquid increases, since there is a limit on the amount of antibacterial agent that can be adsorbed by the pulp fiber, any excess remains as free residue in the treatment wastewater, and if the concentration thereof is high, there is the risk of the appearance of detrimental effects such as eradication of microorganisms used to carry out microbial treatment in the case of treating wastewater with microbial treatment. Accordingly, the amount of cationic antibacterial agent in treatment liquid is preferably 0.03% by weight or less and the amount relative to the pulp fiber is preferably 10% by weight or less. Incidentally, the amount of cationic antibacterial agent relative to the pulp fiber is calculated according to the equation indicated below:

Amount relative to pulp fiber (%)=Amount of antibacterial agent added/treated amount of pulp fiber×100 wherein the treated amount of pulp fiber is based on the dry weight thereof.

A decomposition step may be provided prior to the ozone treatment step for decomposing a used sanitary article into pulp fiber and other materials thereof by allowing a physical force to act on the used sanitary article in an aqueous solution containing a polyvalent metal ion or in an acidic aqueous solution having a pH of 2.5 or lower (to be simply referred to as the "decomposition step").

In this step, a used sanitary article is decomposed into pulp fiber and other materials by allowing a physical force to act on the used sanitary article.

Sanitary articles are normally composed of various materials such as pulp fiber, superabsorbent polymer, non-woven fabric, plastic film and rubber. In this decomposition step, the used sanitary article is decomposed into each of the aforementioned materials. The degree of decomposition is only required to be to a degree that at least a portion of the pulp fiber can be recovered, and is not necessarily required to result in complete recovery of the pulp fiber, and only a portion thereof may be recovered.

Here, there are no particular limitations on the method used to allow physical force to act on the used sanitary article, and examples thereof include agitation, beating, poking, vibrating, tearing, cutting and crushing. Among these, agitation is preferable. Agitation can be carried out in a treatment tank equipped with an agitator in the manner of a washing machine.

This decomposition step is carried out in an aqueous solution containing a polyvalent metal ion or acidic aqueous solution having a pH of 2.5 or lower. The use of an aqueous solution containing polyvalent metal ion or acidic aqueous solution having a pH of 2.5 or lower results in dehydration of the superabsorbent polymer by absorbing water present in the used sanitary article.

Superabsorbent polymers have hydrophilic groups (such as $—COO^-$), and although they are able to absorb a large amount of water as a result of water molecules bonding to the hydrophilic groups by hydrogen bonding, when a superabsorbent polymer that has absorbed water is placed in an aqueous solution containing polyvalent metal ions such as calcium ions, the polyvalent metal ions bond to the hydrophilic groups (such as $—COO^-$) (resulting in the formation of, for example, $—COO—Ca—OCO—$) and hydrogen bonds between the hydrophilic groups and water molecules are severed, thereby resulting in the release of water molecules and dehydration of the superabsorbent polymer. In addition, when a superabsorbent polymer that has absorbed water is placed in an acidic aqueous solution having a pH of 2.5 or lower, since negatively charged hydrophilic groups (such as $—COO^-$) are neutralized by positively charged hydrogen ions ($H^+$) (resulting in the formation of, for example, $—COOH$), the ionic repulsive force of the hydrophilic groups weakens and water absorbency decreases, and this is thought to result in dehydration of the superabsorbent polymer.

Dehydration of the superabsorbent polymer facilitates separation of the pulp fiber and superabsorbent polymer. Although the superabsorbent polymer absorbs water and swells, the solid component concentration in the tank increases, and the treatment efficiency of the mechanical decomposition operation decreases when a used sanitary article is attempted to be decomposed in ordinary water, these can be avoided by carrying out treatment in an aqueous solution containing a polyvalent metal ion or an acidic aqueous solution having a pH of 2.5 or lower.

An ion such as an alkaline earth metal ion or transition metal ion can be used for the polyvalent metal ion.

Examples of alkaline earth metal ions include beryllium, magnesium, calcium, strontium and barium ions. Preferable examples of aqueous solutions containing alkaline earth metal ions include aqueous solutions of calcium chloride, calcium nitrate, calcium hydroxide, calcium oxide, magnesium chloride and magnesium nitrate, and among these, an aqueous calcium chloride solution is particularly preferable.

Although there are no particular limitations on the transition metal ion provided it is able to be incorporated in a superabsorbent polymer, examples thereof include iron, cobalt, nickel and copper ions. Although examples of aqueous solutions containing transition metal ions include aqueous solutions of inorganic acid salts, organic acid salts and complexes of transition metals, from the viewpoints of expense and availability, an aqueous solution of an inorganic acid salt or organic acid salt is preferable. Examples of inorganic acid salts include iron salts such as iron chloride, iron sulfate, iron phosphate or iron nitrate, cobalt salts such as cobalt chloride, cobalt sulfate, cobalt phosphate or cobalt nitrate, nickel salts such as nickel chloride or nickel sulfate, and copper salts such as copper chloride or copper sulfate. Examples of organic acid salts include iron lactate, cobalt acetate, cobalt stearate, nickel acetate and copper acetate.

In the case of using an aqueous solution containing a polyvalent metal ion, an aqueous solution of a calcium compound is preferable in consideration of safety and price. Among calcium compounds, due to the characteristic of the ozone used in the subsequent step ending up being decomposed at alkaline pH, an aqueous solution of weakly alkaline calcium chloride is more preferable than strongly alkaline calcium hydroxide or calcium oxide since it is as close to neutral as possible. Although there are no particular limitations on the pH of the aqueous solution containing polyvalent metal ion, it is preferably 11 or lower. In the case of using an alkaline compound, the pH of the aqueous solution is higher than 7 but not higher than 11.

The amount of polyvalent metal ion is preferably 4 millimoles or more, more preferably 4.5 millimoles to 10 millimoles and even more preferably 5 millimoles to 8 millimoles per 1 g (dry weight) of superabsorbent polymer. If the amount of polyvalent metal ion is excessively low, dehydration of the superabsorbent polymer is inadequate. If the amount of polyvalent metal ion is excessively high, surplus polyvalent metal ion remains in the treatment solution without being incorporated in the superabsorbent polymer, thereby causing the polyvalent metal ion to be wasted and leading to increased treatment cost.

Although there are no particular limitations on the concentration of polyvalent metal ion in the aqueous solution containing polyvalent metal ion provided it allows incorporation of the polyvalent metal ion in the superabsorbent polymer, it is preferably 10 millimoles/liter to 1000 millimoles/liter, more preferably 50 millimoles/liter to 700 millimoles/liter and even more preferably 200 millimoles/liter to 400 millimoles/liter. If the concentration is excessively low, dehydration of the superabsorbent polymer is inadequate. If the concentration is excessively high, surplus polyvalent metal ion remains in the treatment solution without being incorporated in the superabsorbent polymer, thereby causing the polyvalent metal ion to be wasted and leading to increased treatment cost.

When an aqueous calcium chloride solution is used for the aqueous solution containing polyvalent metal ion, although the concentration of calcium chloride is preferably 1% by weight or more, since the effect does not change even if the concentration is increased to 10% by weight or more, a concentration of 1% by weight to 10% by weight and more preferably 3% by weight to 6% by weight.

In the case of using an acidic aqueous solution, the pH of the acidic aqueous solution is 2.5 or lower, preferably 0.5 to 2.5 and more preferably 1.0 to 2.4. If the pH is excessively high, there is the risk of inadequate dehydration of the superabsorbent polymer. If the pH is excessively low, there is the risk of damage to the recovered pulp fiber due to strong acidity.

Although an aqueous solution of an inorganic acid or organic acid can be used for the acidic aqueous solution having a pH of 2.5 or lower provided the pH thereof is 2.5 or lower, an aqueous solution of an organic is somewhat more preferable due to the high level of safety thereof. Although examples of organic acids include tartaric acid, glycolic acid, malic acid, citric acid, succinic acid and acetic acid, citric acid is particularly preferable.

In the case of using an aqueous solution of an organic acid, although there are no particular limitations on the concentration of the organic acid in the aqueous solution provided the pH thereof is 2.5 or lower, the concentration is preferably 0.1% by weight to 10.0% by weight, more preferably 0.5% by weight to 8.0% by weight and even more preferably 1.0% by weight to 5.0% by weight. If the concentration is excessively low, there is the risk of inadequate dehydration of the superabsorbent polymer. If the concentration is excessively high, there is the risk of wasting the organic acid.

Although there are no particular limitations on the amount of aqueous solution used in the decomposition step provided a physical force is able to act on the used sanitary article, the amount is preferably 3 kg to 50 kg and more preferably 3 kg to 10 kg based on 1 kg of soiled used sanitary article. If the amount of aqueous solution is excessively low, the used sanitary article cannot be effectively agitated in the aqueous solution. If the amount of aqueous solution is excessively high, the organic acid is wasted leading to increased treatment cost.

Although there are no particular limitations on the temperature of the aqueous solution used in the decomposition step provided it is a temperature at which the superabsorbent polymer is dehydrated, the temperature is normally higher than 0° C. and lower than 100° C. Although room temperature is sufficient for the temperature of the aqueous solution, the solution may be heated to increase the reaction rate. In the case of heating, the aqueous solution is preferably heated to a temperature of room temperature to 60° C., more preferably room temperature to 40° C. and even more preferably room temperature to 30° C.

Although there are no particular limitations on the duration of the decomposition step provided it is an amount of time sufficient for decomposition of the used sanitary article, it is preferably 5 minutes to 60 minutes, more preferably 10 minutes to 50 minutes and even more preferably 20 minutes to 40 minutes.

When carrying out antibacterial treatment prior to the ozone treatment step, antibacterial treatment can be carried out simultaneously in the decomposition step by adding a cationic antibacterial agent to the solution used in the decomposition step. Namely, when antibacterial treatment is carried out prior to the ozone treatment step, the aqueous solution used in the decomposition step preferably contains a cationic antibacterial agent. Disinfecting using a cationic antibacterial agent for the primary antibacterial agent at the start of treatment makes it possible for the cationic antibacterial agent to be selectively adsorbed onto the anionic pulp fiber, thereby imparting antimicrobial properties to the pulp fiber per se. In addition, when using citric acid for acidic aqueous solution having a pH of 2.5 or lower, due to the favorable compatibility between the quaternary ammonium salt and citric acid, antibacterial action is enhanced by the synergistic effect thereof, thereby making it possible to demonstrate sterilizing effects on viruses and the like for which disinfection is difficult with quaternary ammonium salts alone.

A step for separating pulp fiber from the mixture of pulp fiber and other materials generated in the decomposition step (to be simply referred to as the "separation step") may be provided after the decomposition step.

In the separation step, pulp fiber is separated from the mixture of pulp fiber and other materials such as superabsorbent polymer, non-woven fabric, plastic film or rubber) generated by decomposition of a used sanitary article. In this step, at least a portion of the pulp fiber is separated and recovered. It is not required to recover all of the pulp fiber. In addition, other materials may also be separated and recovered together with the pulp fiber. Although varying according to the separation method, at least a portion of the superabsorbent polymer is normally mixed in with the separated pulp fiber. For example, in a separation method using sieving, a majority of the superabsorbent polymer is mixed in with the separated and recovered pulp fiber in the case of recovering pulp fiber beneath the sieve. In this step, the decomposed constituent materials are preferably separated into a fraction containing pulp fiber and superabsorbent polymer and a fraction containing non-woven fabric, plastic film and rubber. However, a small amount of non-woven fabric, plastic film and rubber may be contained in the fraction containing pulp fiber and superabsorbent polymer, and a small amount of pulp fiber and superabsorbent polymer may be contained in the fraction containing non-woven fabric, plastic film and rubber.

There are no particular limitations on the method used to separate the pulp fiber, and examples thereof include a method consisting of precipitating and separating decomposed constituent materials in water using differences in specific gravity thereof, a method consisting of passing decomposed constituent materials of different sizes through a screen having a prescribed mesh size, and a method consisting of separating with cyclone centrifugal separator.

At least a certain amount of superabsorbent polymer is mixed into the separated pulp fiber. Superabsorbent polymer remaining in the separated pulp fiber is removed by decomposing, lowering molecular weight and solubilizing the superabsorbent polymer in the ozone treatment step following the separation step.

A step may be provided after the ozone treatment step for washing the used sanitary article together with decomposing the used sanitary article into its constituents by agitating the used sanitary article in water or an aqueous solution containing a disinfectant (to simply be referred to as the "washing and decomposition step").

Although the water used in the washing and decomposition step is not necessarily required to contain a disinfectant, an aqueous solution containing a disinfectant may be used. There are no particular limitations on the disinfectant, and examples thereof include chlorine dioxide, acidic electrolyte and ozone water.

In the case of using an aqueous solution containing disinfectant, although there are no particular limitations on the concentration of disinfectant in the aqueous solution containing disinfectant provided disinfection effects are demonstrated, it is preferably 10 ppm by weight to 300 ppm by weight, more preferably 30 ppm by weight to 280 ppm by weight and even more preferably 50 ppm by weight to 250 ppm by weight. If the concentration is excessively low, adequate disinfection effects are not obtained resulting in the risk of bacteria and other microorganisms remaining on the recovered pulp fiber. Conversely, if the concentration is excessively high, not only is disinfectant wasted, but there is also the risk of the disinfectant damaging the pulp fiber and the occurrence of problems with safety.

There are no particular limitations on the type of agitation used in the washing and decomposition step provided sanitary article residue is washed and decomposed into its constituents, and can be carried out using a washing machine, for example. There are also no particular limitations on the agitation conditions provided sanitary article residue is washed and decomposed into its constituents, and for example, the duration of agitation is preferably 5 minutes to 60 minutes, more preferably 10 minutes to 50 minutes and even more preferably 20 minutes to 40 minutes.

In the washing and decomposition step, sanitary article residue from which polymeric absorbents have been removed is washed and the sanitary article is broken up and decomposed into its constituents. Since hot melt adhesive used to join the sanitary article is subjected to oxidative degradation and the adhesive strength between constituents of the sanitary article are weakened in the aforementioned ozone water immersion step, the sanitary article can easily be decomposed into its constituents by agitation in this washing and decomposition step. The sanitary article is also disinfected by disinfectant in the case of using an aqueous solution containing disinfectant.

When carrying out antibacterial treatment after the ozone treatment step, antibacterial treatment can be simultaneously carried out in the washing and decomposition step by adding a cationic antibacterial agent to the aqueous solution containing disinfectant or water used. Namely, when carrying out antibacterial treatment after the ozone treatment step, the aqueous solution containing disinfectant or water used in the washing and decomposition step preferably contains a cationic antibacterial agent. Since the cationic antibacterial agent adsorbs to the pulp fiber and the pulp fiber becomes anionic, the cationic antibacterial agent adsorbed to the pulp fiber is not easily released enabling the cationic antibacterial agent to remain in the ultimately obtained recycled pulp. Even so, when the fiber goes through numerous steps during the time until the final step, small amounts of the cationic antibacterial agent are released in each step, resulting in a decrease in the final content of the cationic antibacterial agent. Thus, antibacterial treatment is preferably carried out at a stage that is as close as possible to the final step from the viewpoint of the content of cationic antibacterial agent in the recycled pulp.

A step for separating pulp fiber from constituents of the used sanitary article following decomposition thereof may be provided after the washing and decomposition step (to simply be referred to as the "pulp fiber separation step").

There are no particular limitations on the method used to separate pulp fiber, and examples thereof include a method consisting of precipitating and separating decomposed constituent materials in water using differences in specific gravity thereof, a method consisting of separating by passing decomposed constituent materials of different sizes through a screen having a prescribed mesh size, and a method consisting of separating with a cyclone centrifugal separator.

A step for washing the separated pulp fiber may be provided after the pulp fiber separation step (to be simply referred to as the "pup fiber washing step").

There are no particular limitations on the method used to wash the separated pulp fiber, and examples thereof include a method consisting of placing the separated pulp fiber in a mesh bag and rinsing the pulp fiber with water.

A step for dehydrating the washed pulp fiber may be optionally provided after the pulp fiber washing step (to be simply referred to as the "pulp fiber dehydration step").

There are no particular limitations on the method used to dehydrate the washed pulp fiber, and examples thereof include a method consisting of spin-drying the washed pulp fiber placed in a mesh bag with a spin dryer.

The pulp fiber washing step and pulp fiber dehydration step may be carried out one time each or may be alternately repeated several times.

A step for drying the dehydrated pulp fiber may be optionally provided after the pulp fiber dehydration step (to be simply referred to as the "pulp fiber drying step"). Since pulp fiber obtained according to the method of the present invention is resistant to mold growth even in a damp state, it is not necessarily required to provide the drying step since the pulp fiber can be stored in a damp state without drying.

The method of the present invention can further comprise a step for separating and recovering plastic materials (to be simply referred to as the "plastic material separation and recovery step"). Here, plastic materials refer to materials such as non-woven fabric materials, film materials or elastomer materials. The plastic material separation and recovery step can be carried out in parallel with the pulp fiber separation step after the aforementioned washing and decomposition step. The plastic material separation and recovery step can comprise a washing step, dehydration step and drying step similar to the aforementioned pulp fiber washing step, pulp fiber dehydration step and pulp fiber drying step. The recovered plastic material can be used as solid fuel, for example, after undergoing RPF treatment.

The following indicates typical examples of process flows for manufacturing recycled pulp from a used sanitary article using the method of the present invention. However, the present invention is not limited to the following examples.

Process Flow Example 1

(1) Decomposition step for decomposing a used sanitary article into pulp fiber and other materials by allowing physical force to act on the used sanitary article in an aqueous solution containing a polyvalent metal ion or an acidic aqueous solution having a ph of 2.5 or lower containing a cationic antibacterial agent.

(2) Ozone treatment step for decomposing superabsorbent polymer adhered to the pulp fiber by immersing the pulp fiber in an ozone-containing aqueous solution.

(3) Step for washing and recovering the pulp fiber.

Process Flow Example 2

(1) Decomposition step for decomposing a used sanitary article into pulp fiber and other materials by allowing physical force to act on the used sanitary article in an aqueous solution containing a polyvalent metal ion or an acidic aqueous solution having a of 2.5.

(2) Ozone treatment step for decomposing superabsorbent polymer adhered to the pulp fiber by immersing the pulp fiber in an ozone-containing aqueous solution containing a cationic antibacterial agent.

(3) Step for washing and recovering the pulp fiber.

Process Flow Example 3

1. Ozone treatment step for decomposing superabsorbent polymer in a used sanitary article by immersing the used sanitary article in an ozone-containing aqueous solution containing a cationic antibacterial agent.

2. Step for washing the used sanitary article and decomposing the used sanitary article into its constituents by agitating the used sanitary article in an aqueous solution containing disinfectant or in water.

3. Step for separating and recovering pulp fiber.

Process Flow Example 4

1. Ozone treatment step for decomposing superabsorbent polymer in a used sanitary article by immersing the used sanitary article in an ozone-containing aqueous solution.

2. Step for washing the used sanitary article and decomposing the used sanitary article into its constituents by agitating the used sanitary article in an aqueous solution containing disinfectant or water containing a cationic antibacterial agent.

3. Step for separating and recovering pulp fiber.

The following provides a detailed description of the aforementioned Process Flow Example 1.

(1) A used disposable diaper is weighed (weighing step).

(2) The used disposable diaper and an aqueous solution (pH 2.2) containing 1% by weight of citric acid and 0.003% by weight of benzalkonium chloride are charged into a washing machine (primary disinfection and adsorption of antibacterial agent onto pulp fiber) followed by decomposing the diaper using impacts generated by agitation while washing according to the operating procedure of an upright washing machine (decomposition step).

(3) The diaper is separated into a fraction containing pulp fiber and superabsorbent polymer and a fraction containing non-woven fabric, plastic film and rubber (separation step).

(4) The recovered pulp fiber and superabsorbent polymer are dehydrated (dehydration step).

(5) The dehydrated pulp fiber and superabsorbent polymer are immersed in an aqueous solution of an organic acid (such as citric acid) having a pH of 2.5 or lower (calcium removal and acidification) followed by subjecting to ozone treatment under acidic conditions resistant to deactivation of ozone (dissolution of superabsorbent polymer, secondary disinfection, bleaching and deodorization) (ozone treatment step).

(6) Dehydration, washing and pH adjustment
(7) Recovery of pulp fiber
(8) Dehydration step
(9) Drying step (tertiary disinfection)

The pulp fiber can be stored in a damp state even in the absence of tertiary disinfection since they have antibacterial properties.

The ash content of recycled pulp obtained according to the method of the present invention is preferably 0.65% by weight or less. In addition, since contaminants contained in unused pulp can also be removed by treating with an ozone-containing aqueous solution having a pH of 2.5 or lower, recycled pulp can be obtained that has lower ash content than unused pulp. The ash content of recycled pulp obtained according to the present invention is more preferably 0.11% by weight or less and even more preferably 0.05% by weight to 0.11% by weight.

Furthermore, the method used to measure ash content is as indicated below.

[Ash Content]

Ash content refers to the amount of inorganic matter or incombustible residue remaining after organic matter has been asked. Ash content is measured in accordance with the contents of "5. Ash Test Method" of "2. General Test Methods" defined in the Japanese Specifications of Sanitary Napkin Materials. Namely, ash content is measured in the manner indicated below.

After preliminarily subjecting a platinum, quartz or porcelain crucible to intense heating for 1 hour at 500° C. to 550° C. and allowing to cool on standing, the weight thereof is measured precisely. 2 to 4 g of sample are then collected and placed in the crucible followed by precisely measuring the weight thereof, and after removing or shifting the cover of the crucible, the sample is initially subjected to mild heating followed by gradually raising the temperature and subjecting to intense heating for 4 hours at 500° C. to 550° C. to ash the sample until carbides no longer remain. After allowing to cool on standing, the weight thereof is measured precisely. After again ashing the residue to a constant weight and allowing to cool on standing, the weight thereof is measured precisely and used as the amount of ash (%).

Recycled pulp obtained according to the method of the present invention preferably has an antibacterial activity value of 2.0 or more. The antibacterial activity value of the recycled pulp is more preferably 4.5 or more and even more preferably 5.5 or more. Antibacterial activity value is measured in accordance with JIS Z 2801.

Since recycled pulp obtained according to the method of the present invention has a low ash content and high antibacterial activity value, it can be used as recycled pulp capable of being used in sanitary articles.

Recycled pulp obtained according to the method of the present invention is preferably used in at least one of an absorbent of a sanitary article, tissue and non-woven fabric.

EXAMPLES

The ozone water generator and physiological saline were used in the following examples and comparative examples.

[Ozone Water Generator]
Manufacturer: Mitsubishi Electric Corp.
Name: Ozone water generator
Model: OS-25V
Variable ozone water concentration range: 1 mg/m$^3$ to 80 mg/m$^3$
Ozone water exposure tank volume: 30 L
[Physiological Saline]
Concentration: 0.9% saltwater

Example 1

After immersing a commercially available disposable diaper (Moony®, Unicharm Corp., M size) in 3 L of physiological saline for 10 minutes and allowing to absorb water, the disposable diaper was immersed for 10 minutes in 3 L of an aqueous solution (pH 2.2) obtained by dissolving 1% by weight of citric acid and 0.003% by weight of benzalkonium chloride therein to inhibit swelling of superabsorbent polymer in the disposable diaper and allow the benzalkonium chloride to be adsorbed by pulp fiber. The disposable diaper was then taken out of the solution and placed in a mesh bag (measuring 30 cm on a side, N-No. 250HD, NBC Meshtec Inc.) followed by spin-drying for 5 minutes in the spin-drying tub of a twin tub compact washing machine (Harebare AST-01, Alumis Co., Ltd.) to remove excess water retained by the pulp, break up the disposable diaper and separate the absorbent portion thereof, and then carrying out treatment consisting of blowing in ozone gas having a concentration of 80 mg/m$^3$ for 30 minutes after placing in 20 L of a 1% by weight aqueous citric acid solution (pH 2.2). The amount of dissolved ozone in the treatment water after 30 minutes was 30 ppm by weight and the pH of the treatment solution was 2.4. As a result of straining the treatment water through a mesh having openings measuring 2 mm×2 mm, the super absorbent polymer was no longer present and pulp and other plastic materials were able to be recovered. This recovered pulp was placed in a mesh bag (measuring 30 cm on a side, N-No. 250HD, NBC Meshtec Inc.) and rinsed for 15 minutes with tap water followed by spin-drying for 5 minutes in the spin-drying tub to obtain recycled pulp.

As a result of analyzing the ash content of this recycled pulp according to the contents of "5. Ash Test Method" of "2. General Test Methods" defined in the Japanese Specifications of Sanitary Napkin Materials, the ash content was determined to be able to be reduced to 0.12%. Furthermore, the ash content of the pulp originally contained in the commercially available disposable diaper used in the examples and comparative examples (to also be referred to as "unused pulp") was 0.18% by weight. As a result of this treatment, it was determined to be possible to remove residual contaminants down to the level of fine residual contaminants originally contained in the unused pulp, thereby making it possible to obtain recycled pulp having a lower ash content than unused pulp.

As a result of evaluating the antibacterial properties of the resulting recycled pulp in accordance with JIS Z 2801, the antimicrobial activity value for *Escherichia coli* strain NBRC3972 was 6.08 or more and the antimicrobial activity value for *Staphylococcus aureus* strain NBRC12732 was 5.74 or more (an antimicrobial activity value of 2.0 or more is considered to constitute antibacterial efficacy). In addition, as a result of placing the recycled pulp following the aforementioned spin-drying in a Tupperware container ("Firmly Pack R", Nakaya Kagaku Sangyo Co., Ltd.) and storing for 30 days in a constant temperature bath at 30° C., visible mold growth was not confirmed.

Example 2

After immersing a commercially available disposable diaper (Moony®, Unicharm Corp., M size) in 3 L of physiological saline for 10 minutes and allowing to absorb water, the disposable diaper was immersed for 10 minutes in 3 L of an aqueous solution (pH 2.2) obtained by dissolving 1% by weight of citric acid and 0.003% by weight of cetylpyridinium chloride therein to inhibit swelling of superabsorbent polymer in the disposable diaper and allow the cetylpyridinium chloride to be adsorbed by pulp fiber. The disposable diaper was then taken out of the solution and placed in a mesh bag (measuring 30 cm on a side, N-No. 250HD, NBC Meshtec Inc.) followed by spin-drying for 5 minutes in the spin-drying tub of a twin tub compact washing machine (Harebare AST-01, Alumis Co., Ltd.) to remove excess water retained by the pulp, break up the disposable diaper and separate the absorbent portion thereof, and then carrying out treatment consisting of blowing in ozone gas having a concentration of 80 mg/m$^3$ for 30 minutes after placing in 20 L of a 1% by weight aqueous citric acid solution (pH 2.2). The amount of dissolved ozone in the treatment water after 30 minutes was 30 ppm by weight and the pH of the treatment solution was 2.4. As a result of straining the treatment water through a mesh having openings measuring 2 mm×2 mm, the superabsorbent polymer was no longer present and pulp and other plastic materials were able to be recovered. This recovered pulp was placed in a mesh bag (measuring 30 cm on a side, N-No. 250HD, NBC Meshtec. Inc.) and rinsed for 15 minutes with tap water followed by spin-drying for 5 minutes in the spin-drying tub to obtain recycled pulp.

As a result of analyzing the ash content of this recycled pulp according to the contents of "5. Ash Test Method" of "2. General Test Methods" defined in the Japanese Specifications of Sanitary Napkin Materials, the ash content was determined to be able to be reduced to 0.11%. As a result of this treatment, it was determined to be possible to remove residual contaminants down to the level of fine residual contaminants originally contained in the unused pulp, thereby making it possible to obtain recycled pulp having a lower ash content than unused pulp.

As a result of evaluating the antibacterial properties of the resulting recycled pulp in accordance with JIS Z 2801, the antimicrobial activity value for *Escherichia coli* strain NBRC3972 was 6.08 or more and the antimicrobial activity value for *Staphylococcus aureus* strain NBRC12732 was 5.74 or more. In addition, as a result of placing the recycled pulp following the aforementioned spin-drying in a Tupperware container ("Firmly Pack R", Nakaya Kagaku Sangyo Co., Ltd.) and storing for 30 days in a constant temperature bath at 30° C., visible mold growth was not confirmed.

Comparative Example 1

After allowing commercially available disposable diapers (Moony®, Unicharm Corp., M size) to absorb 200 mL of physiological saline, eight of the disposable diapers were placed in a twin tub compact washing machine (Harebare AST-01, Alumis Co., Ltd.) followed by adding 80 g of calcium oxide (CaO) (Wako Pure Chemical Industries, Ltd.) and then adding 6.5 L of an aqueous sodium hypochlorite solution having a concentration of 250 ppm by weight (obtained by diluting sodium hypochlorite manufactured by Wako Pure Chemical Industries, Ltd. with tap water). After washing for 15 minutes, the liquid inside the washing tub was drained followed by again adding 6.5 L of aqueous sodium hypochlorite solution having a concentration of 250 ppm by weight (obtained by diluting sodium hypochlorite manufactured by Wako Pure Chemical Industries, Ltd. with tap water). After washing for 15 minutes, only the pulp floating in the liquid inside the washing tub was skimmed off and placed in a mesh bag (measuring 30 cm on a side, N-No. 250HD, NBC Meshtec Inc.) followed by spin-drying for 5 minutes in the spin-drying tub. The recovered pulp was rinsed with tap water for 15 minutes while still in the mesh bag and again spun-dried for 5 minutes in the spin-drying tub. The recovered pulp was then dried at 105° C. for 24 hours with a hot air dryer.

As a result of evaluating the antibacterial properties of the resulting recycled pulp in accordance with JIS Z 2801, the antimicrobial activity value for *Escherichia coli* strain NBRC3972 was 4.05 and the antimicrobial activity value for *Staphylococcus aureus* strain NBRC12732 was 3.02 or more. In addition, as a result of placing the recycled pulp following the aforementioned spin-drying in a Tupperware container ("Firmly Pack R", Nakaya Kagaku Sangyo Co., Ltd.) and storing for 30 days in a constant temperature bath at 30° C., visible mold growth was confirmed after 3 days and a large amount of mold was confirmed to have grown after 30 days. Although safety (hygiene) was able to be ensured in Comparative Example 1 as well, there was the problem of the occurrence of mold growth soon after storing in a damp state.

Comparative Example 2

After immersing a commercially available disposable diaper (Moony®, Unicharm Corp., M size) in 3 L of physiological saline for 10 minutes and allowing to absorb water, the disposable diaper was immersed for 10 minutes in 3 L of aqueous citric acid solution (pH 2.2) having a concentration of 1% by weight to inhibit swelling of superabsorbent polymer in the disposable diaper. The disposable diaper was then taken out of the solution and placed in a mesh bag (measuring 30 cm on a side, N-No. 250HD, NBC Meshtec Inc.) followed by spin-drying for 5 minutes in the spin-drying tub of a twin tub compact washing machine (Harebare AST-01, Alumis Co., Ltd.) to remove excess water retained by the pulp, break up the disposable diaper and separate the absorbent portion thereof, and then carrying out treatment consisting of blowing in ozone gas having a concentration of 80 mg/m$^3$ for 30 minutes after placing in 20 L of a 1% by weight aqueous citric acid solution (pH 2.2). The amount of dissolved ozone in the treatment water after 30 minutes was 30 ppm by weight and the pH of the treatment solution was 2.4. As a result of straining the treatment water through a mesh having openings measuring 2 mm×2 mm, the superabsorbent polymer was no longer present and pulp and other plastic materials were able to be recovered. This recovered pulp was placed in a mesh bag (measuring 30 cm on a side, N-No. 250HD, NBC Meshtec Inc.) and rinsed for 15 minutes with tap water followed by spin-drying for 5 minutes in the spin-drying tub to obtain recycled pulp. As a result of analyzing the ash content of this recycled pulp according to the contents of "5. Ash Test Method" of "2. General Test Methods" defined in the Japanese Specifications of Sanitary Napkin Materials, the ash content was determined to be able to be reduced to 0.13%. As a result of evaluating the antibacterial properties of the resulting pulp fiber in accordance with JIS Z 2801, the antimicrobial activity value for *Escherichia coli* strain NBRC3972 was 4.25 and the antimicrobial activity value for *Staphylococcus aureus* strain NBRC12732 was 3.74. In addition, as a result of placing the recycled pulp following the aforementioned spin-drying in a Tupperware container ("Firmly Pack R", Nakaya Kagaku Sangyo Co., Ltd.) and storing for 30 days in a constant temperature bath at 30° C., visible mold growth was confirmed after 7 days and a large amount of mold was confirmed to have grown after 30 days. Although safety (hygiene) was able to be ensured in Comparative Example 2 as well, there was the problem of the occurrence of mold growth soon after storing in a damp state.

INDUSTRIAL APPLICABILITY

Recycled pulp manufactured according to the method of the present invention can be preferably reused in the manufacturing of sanitary articles.

The invention claimed is:

1. A method for manufacturing recycled pulp able to be reused in sanitary articles by recovering pulp fiber from a used sanitary article, the method comprising:
  performing an ozone treatment step comprising:
    immersing, in an ozone-containing aqueous solution, the used sanitary article that comprises pulp fiber; and
    decomposing, using ozone in the ozone-containing aqueous solution, superabsorbent polymer that is either present in the used sanitary article or adhered to the pulp fiber; and
  treating the used sanitary article or pulp fiber with a cationic antibacterial agent either before, simultaneous to or after the ozone treatment step, wherein
  the decomposed superabsorbent polymer is discharged with the ozone-containing aqueous solution, and
  the ozone treatment step causes the superabsorbent polymer to decrease in molecular weight and become solubilized so that the superabsorbent polymer is decomposed.

2. The method according to claim 1, comprising a decomposition step for decomposing a used sanitary article into pulp fiber and other materials by allowing physical force to act on the used sanitary article in an aqueous solution containing a polyvalent metal ion or an acidic aqueous solution having a pH of 2.5 or lower prior to the ozone treatment step.

3. The method according to claim 2, wherein the aqueous solution containing a polyvalent metal ion or the acidic aqueous solution having a pH of 2.5 or lower contains a cationic antibacterial agent.

4. The method according to claim 3, wherein the ozone-containing aqueous solution contains a cationic antibacterial agent.

5. The method according to claim 3, wherein the cationic antibacterial agent is a quaternary ammonium salt.

6. The method according to claim 2, wherein the polyvalent metal ion is an alkaline earth metal ion.

7. The method according to claim 2, wherein the ozone-containing aqueous solution contains a cationic antibacterial agent.

8. The method according to claim 2, wherein the cationic antibacterial agent is a quaternary ammonium salt.

9. The method according to claim 1, comprising a step for washing a used sanitary article and decomposing the used sanitary article into constituents thereof by agitating the used sanitary article in an aqueous solution containing a disinfectant or in water after the ozone treatment step.

10. The method according to claim 9, wherein the aqueous solution containing a disinfectant or the water contains a cationic antibacterial agent.

11. The method according to claim 10, wherein the ozone-containing aqueous solution contains a cationic antibacterial agent.

12. The method according to claim 9, wherein the ozone-containing aqueous solution contains a cationic antibacterial agent.

13. The method according to claim 9, wherein the cationic antibacterial agent is a quaternary ammonium salt.

14. The method according to claim 1, wherein the ozone-containing aqueous solution contains a cationic antibacterial agent.

15. The method according to claim 1, wherein the cationic antibacterial agent is a quaternary ammonium salt.

16. The method according to claim 1, wherein the ozone-containing aqueous solution contains an organic acid and the pH of the ozone-containing aqueous solution is 2.5 or lower.

17. The method according to claim 1, wherein the concentration of ozone in the ozone-containing aqueous solution is 1 ppm by weight to 50 ppm by weight.

18. A recycled pulp obtained according to the method according to claim 1, having an ash content of 0.65% by weight or less.

19. The recycled pulp according to claim 18, having an antibacterial activity value of 2.0 or more.

* * * * *